United States Patent [19]
Iglesias

[11] 4,190,051
[45] Feb. 26, 1980

[54] LITHOTRITE FOR ELECTROHYDRAULIC CYSTOLITHOTRIPSY

[76] Inventor: Jose J. Iglesias, 1341 North Ave., Elizabeth, N.J. 07603

[21] Appl. No.: 913,112

[22] Filed: Jun. 6, 1978

[51] Int. Cl.² ............................................. A61B 17/22
[52] U.S. Cl. ................................................... 128/328
[58] Field of Search ................... 128/328, 244, 303.14, 128/303.15, 303.17

[56] References Cited

U.S. PATENT DOCUMENTS

| | | | |
|---|---|---|---|
| 2,275,167 | 3/1942 | Bierman | 128/303.17 |
| 3,735,764 | 5/1973 | Balev et al. | 128/328 |
| 3,856,015 | 12/1974 | Iglesias | 128/303.15 |
| 3,902,499 | 9/1975 | Shene | 128/328 |

FOREIGN PATENT DOCUMENTS

| | | | |
|---|---|---|---|
| 2635635 | 2/1978 | Fed. Rep. of Germany | 128/328 |
| 221209 | 10/1968 | U.S.S.R. | 128/328 |

*Primary Examiner*—Lee S. Cohen
*Attorney, Agent, or Firm*—Scrivener, Parker, Scrivener and Clarke

[57] ABSTRACT

A lithotrite which forms part of an instrument used by urologists for crushing concretions in the urinary tract is provided by the invention as a modified form of the cutting loop of a resectoscope, which is an instrument normally used in transurethral resection procedures.

3 Claims, 6 Drawing Figures

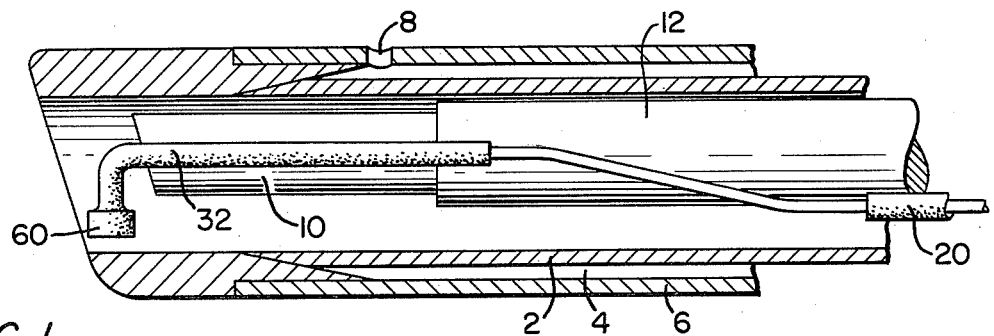
FIG. 1.
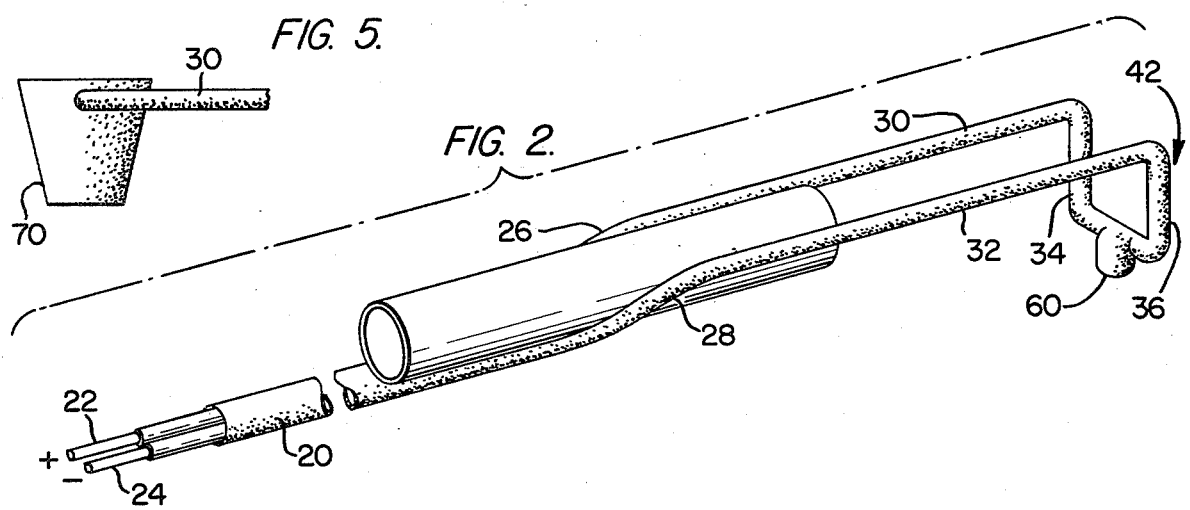
FIG. 2.
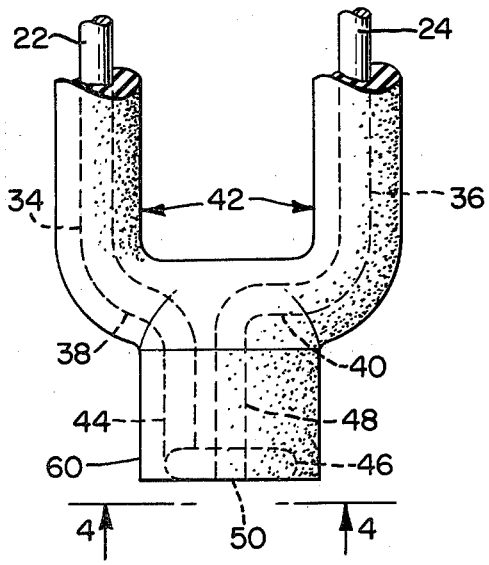
FIG. 3.
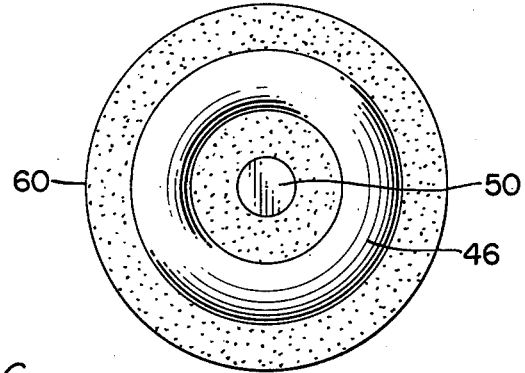
FIG. 4.
FIG. 5.
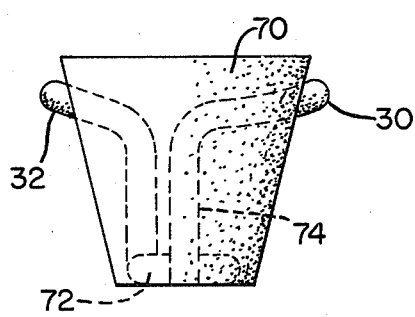
FIG. 6.

LITHOTRITE FOR ELECTROHYDRAULIC CYSTOLITHOTRIPSY

FIELD OF THE INVENTION

This invention relates boradly to the field and science of urology and, more particularly, to systems and instruments for disintegrating calculi in the urinary tract by hydraulic impacts produced by an electrical discharge in the liquid medium which surrounds the calculi and, more specifically, to the lithotrite which forms part of such a system and carries the electrical poles across which the discharge is generated.

STATE OF THE PRIOR ART

Systems for effecting the described procedure are disclosed in U.S. Pat. Nos. 3,557,793, issued Jan. 26, 1971 to Ediny, Balaev and Gostkin, 3,735,764, issued May 29, 1973 to Balev, Ediny and Kerol, and 3,902,499, issued Sept. 2, 1975 to Shene, and are described in the article entitled Electrohydraulic Cystolithotripsy by Alex M. Raney, M.D. in Urology, April, 1976, Vol. VII, No. 4. Known lithotrites are either flexible or rigid, but in all cases are formed as coaxial conductors insulated from each other and, with the insulating material, forming a tubular unit which is introduced into and through the urethra in a position parallel to the direction of the urethra. Such lithotrities do not permit adequate manipulation of the calculi within the bladder because of the linear position of the lithotrite. Further, if the lithotrite is flexible it is impossible to manipulate the stone, and the lithotrite may slip around the stone during disintegration with consquent injury to the bladder mucosa and cloudiness of the irrigant, necessitating interruption of the procedure. In addition, in using known lithotrites it is impossible, because of their configuration and their position in use, for the surgeon to visualize the contact of the tip of the lithotrite with the stone or to have a solid contact with the stone, which is most desirable in moving the stone or its parts after it has been broken.

The resectoscope is another instrument which is well known to the urological arts and is used to perform transurethral resections. A special form of this instrument is described and claimed in my U.S. Pat. No. 3,835,842, issued Sept. 17, 1974, for Endoscope with Continuous Irrigation, and is constructed and operative to provide continuous inflow of clear irrigant to the operative field and continuous outflow of turbid fluid from the operative field with resultant continuous clear vision of the operative field. Resectoscopes of all types include a part known as a cutting loop which is linearly manipulated by the surgeon during the operative procedure to perform the resection.

SUMMARY OF THE INVENTION

The invention consists in the provision of a lithotrite having the general configuration of the cutting loop of a resectoscope and constructed and adapted to replace the cutting loop in a resectoscope for linear manipulation, and having at its distal end a rigid, depending part which presents the electrodes to the fluid immersing the calculi and, in addition, provides a means for manipulating the calculi.

BRIEF DESCRIPTION OF THE DRAWINGS

FIG. 1 is a longitudinal sectional view of the distal end of a resectoscope showing in elevation the distal end of the lithotrite provided by the invention;

FIG. 2 is a perspective view of a lithotrite according to the invention;

FIG. 3 is an enlarged end view of the distal end of the lithotrite of FIG. 2, and FIG. 4 is an enlarged view taken on line 4—4 of FIG. 3, and FIGS. 5 and 6, are respectively, a side elevational view and an end view of the distal end of a second embodiment of the invention.

DESCRIPTION OF THE INVENTION

In FIG. 1 of the drawings there is disclosed the distal end part of a resectoscope and, more particularly, a resectoscope of the type which is constructed and operative to provide constant inflow of clear irrigant to the operative field through a central tube 2 and to provide constant outflow of turbid fluid from the operative field through the annular passage 4 between the exterior of tube 2 and the interior wall of sheath 6, there being one or more inlet openings 8 leading to the outflow passage. A telescope 10, a tube 12 which surrounds the telescope, and a cutting loop (not shown) are also provided. These parts are conventional and form parts of the resectoscope with continuous clear vision at the operative field which is disclosed and claimed in my U.S. patent which is referred to above. It will be understood, however, that the invention described and claimed herein is useful with any type of resectoscope and is disclosed herein in connection with my patented resectoscope only for purposes of illustration.

The lithotrite provided by the invention is used as a part of a resectoscope when it is desired to disintegrate calculi in the urinary tract and, on such occasion, the usual cutting loop of the resectoscope is removed and is replaced by the lithotrite provided by this invention.

This lithotrite comprises at least one elongated hollow stem 20 through which there extend two wires 22, 24 which, at a point proximal to the end of the stem 20, are connected to positive and negative sources of electrical energy. These wires extend through the stem and emerge from the distal end thereof to provide upwardly and outwardly extending parts 26, 28 and, distal thereto, parallel parts 30, 32.

At the distal ends of the parallel parts the wires extend downwardly at preferably right angles to the parallel parts, as shown at 34, 36 and then toward each other, as shown at 38, 40, thus forming a depending generally U-shaped loop 42 at the distal end of the lithotrite. The terminal end of wire 22 continues beyond its parts 34, 38 and depends from the bottom of the loop, forming a straight downwardly extending section 44 which at its lower end is turned at right angles to form a circular loop 46 the plane of which is generally parallel to the bottom of the U-shaped loop 42. The terminal end of wire 24 continues beyond its parts 36, 40 and depends from the bottom of the loop, forming a straight section 48 which is parallel to part 44 of wire 22 and the end 50 of which terminates within and concentric with the loop 46 of wire 22.

All parts of the wires 22, 24 are electrically insulated, the electrical insulation being most clearly shown in the drawings as applied to those parts of the wires which are distal to the distal end of the stem 20. These parts of the wires, including the depending loop 42 and the parts 34, 38, 44 and 46 of wire 22 and parts 36, 40, 48 and 50 of wire 24 are entirely encased in electrical insulating material, and the parts of the wires at the center of the depending loop 42 are encased in insulating material which forms a depending cylindrical member 60 within which the terminal parts of the two wires are embedded, with the exception of the exposed lower surface of the loop 46 of wire 22 and the exposed end 50 of wire 24.

The depending cylindrical member 60 is particularly useful in manipulating a large stone during the operative procedure. However, the calculi is often of small size and, in accordance with a modified form of the invention, the distal end of the instrument is provided with a member having a small lower end within which the concentric loop and wire are embedded. This embodiment of the invention is disclosed in FIGS. 5 and 6, and it will be seen that it comprises a member 70 of preferably circular cross-section and inverted frusto-conical shape which is positioned between and supported by the distal ends of the spaced parallel sections 30, 32 of the insulated wires which protrude from the distal end of the stem 20. The end of wire 32 extends downwardly within the member 70 and at its lower end is formed into a circular loop 72 the lower surface of which lies within the lower surface of the member 70 and is exposed, while the end of the wire 30 extends downwardly within the member 70 to form a vertical part 74 the lower end of which is within and concentric with the open loop 72 and the end surface of which lies within the lower surface of the member 70 and is exposed. Because of the reduced transverse size of the lower end of member 70 a small calculi may be more easily seen during the operative procedure.

When it is desired to effect disintegration of calculi in the urinary tract by hydraulic impacts produced by an electrical discharge in the liquid medium which surrounds the calculi the usual cutting loop of the resectoscope is removed and replaced by the lithotrite provided by the invention, and the wires are connected to positive and negative sources of electrical energy to perform the disintegration in known manner. The surgeon may now reciprocate the lithotrite longitudinally of the resectoscope with the distal end of the lithotrite within the operative field in order to disintegrate calculi, and the depending member 60 or 70 may be employed to move, manipulate, dislodge and remove the calculi.

It will be understood that while the invention has been described herein as having a single stem through which two wires extend, it may take the form of the well known resectoscope manufactured by Karl Storz KG which has two laterally spaced stems through each of which a wire extends. Accordingly, the phrase "at least one stem" is used in the appended claims to denote either type of lithotrite.

I claim:

1. A lithotrite for use in an electrohydraulic system for disintegrating bladder calculi in situ, comprising at least one elongated hollow stem having proximal and distal ends, two electro-conductive wires extending longitudinally within the stem and at the proximal end of the stem being adapted for connection, respectively, to the positive and negative terminals of a source of direct current, each wire having a part protruding from the distal end of the stem, the protruding parts of the wires being rigid and comprising parallel sections adjacent the distal end of the stem and parts depending from the parallel sections distal to the distal end of the stem, the depending part of one wire being formed at its lower end as a horizontal open loop, the depending part of the other wire being vertical with its lower end within and concentric with the open loop of the one wire, and electrical insulating material surrounding all parts of the wires distal of the stem except only the lower surface of the open loop and the lower end surface of the other wire which is within and concentric with the open loop.

2. A lithotrite according to claim 1, in which the depending parts of the wires together form a U-shaped loop having at the center of its lower part a depending cylindrical member formed of said insulating material, and the open loop of the one wire and the depending part of the other wire are embedded in the depending cylindrical member.

3. A lithotrite according to claim 1, in which an inverted frusto-conical member formed of said insulating material is positioned between and supported by the parallel sections of the wires, and the depending parts of the two wires which form the open loop and the vertical wire are embedded in the frusto-conical member.

* * * * *